(12) United States Patent
Viswanathan

(10) Patent No.: US 12,558,157 B2
(45) Date of Patent: Feb. 24, 2026

(54) APPARATUS AND METHODS FOR PULSED FIELD ABLATION INCLUDING COMPRESSIBLE ELECTRODES

(71) Applicant: Alpfa Medical, Inc., Menlo Park, CA (US)

(72) Inventor: Raju Viswanathan, Palo Alto, CA (US)

(73) Assignee: Alpfa Medical, Inc., Menlo Park, CA (US)

( * ) Notice: Subject to any disclaimer, the term of this patent is extended or adjusted under 35 U.S.C. 154(b) by 0 days.

(21) Appl. No.: 18/999,981

(22) Filed: Dec. 23, 2024

(65) Prior Publication Data

US 2025/0120764 A1    Apr. 17, 2025

Related U.S. Application Data

(63) Continuation of application No. PCT/US2023/068807, filed on Jun. 21, 2023.

(Continued)

(51) Int. Cl.
*A61B 18/18* (2006.01)
*A61B 18/14* (2006.01)
*A61B 18/00* (2006.01)

(52) U.S. Cl.
CPC *A61B 18/1492* (2013.01); *A61B 2018/00083* (2013.01); *A61B 2018/00267* (2013.01);
(Continued)

(58) Field of Classification Search
CPC ...... A61B 18/1492; A61B 2018/00267; A61B 2018/00577; A61B 5/287; A61B 5/6858;
(Continued)

(56) References Cited

U.S. PATENT DOCUMENTS 5,476,495 A * 12/1995 Kordis ................... A61B 5/287
                                                            600/374
5,494,042 A *  2/1996 Panescu ............... A61B 5/6855
                                                            600/374
(Continued)

FOREIGN PATENT DOCUMENTS

EP           1613387 B1     1/2008
WO      WO-2016060983 A1    4/2016
(Continued)

OTHER PUBLICATIONS

International Preliminary Report on Patentability for International Application No. PCT/US2023/068807 mailed Jan. 2, 2025, 12 pages.

(Continued)

*Primary Examiner* — Michael F Peffley
*Assistant Examiner* — Amanda L Zink
(74) *Attorney, Agent, or Firm* — Cooley LLP

(57) ABSTRACT

Systems, devices, and methods described herein relate to catheter devices for therapy delivery in renal denervation applications. In some embodiments, a catheter includes a shaft having first and second sets of electrodes. In some embodiments, each electrode set can include electrodes that are spaced from one another by inter-electrode spacings and being spaced from one another by an inter-set spacing. In some embodiments, the inter-set spacing can be at least 50% greater than each inter-electrode spacing. In some embodiments, the first or second set of electrodes can include at least one basket electrode.

29 Claims, 11 Drawing Sheets

Related U.S. Application Data

(60) Provisional application No. 63/354,133, filed on Jun. 21, 2022.

(52) U.S. Cl.
CPC .............. *A61B 2018/00577* (2013.01); *A61B 2018/00696* (2013.01); *A61B 2018/1467* (2013.01)

(58) Field of Classification Search
CPC ........... A61B 2018/00214; A61B 2018/00351; A61B 2018/1467; A61B 2218/002; A61B 5/6859
See application file for complete search history.

(56) References Cited

U.S. PATENT DOCUMENTS

| | | | |
|---|---|---|---|
| 5,904,680 A * | 5/1999 | Kordis | A61B 5/6858 606/41 |
| 6,086,532 A * | 7/2000 | Panescu | A61B 5/7435 600/437 |
| 7,070,596 B1 | 7/2006 | Woloszko et al. | |
| 8,048,067 B2 | 11/2011 | Davalos et al. | |
| 8,504,147 B2 | 8/2013 | Deem et al. | |
| 8,870,863 B2 | 10/2014 | Leung et al. | |
| 9,387,031 B2 | 7/2016 | Stewart et al. | |
| 10,136,942 B1 | 11/2018 | Cosman, Jr. et al. | |
| 10,722,288 B2 | 7/2020 | Wu et al. | |
| 10,893,905 B2 | 1/2021 | Viswanathan et al. | |
| 11,633,230 B2 | 4/2023 | Stewart et al. | |
| 11,974,804 B2 | 5/2024 | Zarins et al. | |
| 12,076,072 B2 | 9/2024 | Athos et al. | |
| 12,114,919 B2 | 10/2024 | Forsyth et al. | |
| 12,150,698 B2 | 11/2024 | Viswanathan et al. | |
| 12,239,364 B2 | 3/2025 | Govari et al. | |
| 2001/0012934 A1 | 8/2001 | Chandrasekaran et al. | |
| 2002/0087208 A1 | 7/2002 | Koblish et al. | |
| 2011/0087211 A1 | 4/2011 | Kulesa et al. | |
| 2012/0157993 A1 | 6/2012 | Jenson et al. | |
| 2012/0265198 A1 * | 10/2012 | Crow | A61B 18/1492 606/41 |
| 2013/0030430 A1 | 1/2013 | Stewart et al. | |
| 2015/0289929 A1 | 10/2015 | Toth et al. | |
| 2016/0113709 A1 * | 4/2016 | Maor | A61B 18/1492 606/41 |
| 2017/0065339 A1 * | 3/2017 | Mickelsen | A61N 1/327 |
| 2018/0117287 A1 | 5/2018 | Krautkremer et al. | |
| 2019/0298442 A1 | 10/2019 | Ogata et al. | |
| 2020/0205892 A1 | 7/2020 | Viswanathan et al. | |
| 2021/0085387 A1 * | 3/2021 | Amit | A61B 18/1492 |
| 2021/0161582 A1 * | 6/2021 | Byrd | A61B 18/1206 |
| 2023/0054269 A1 | 2/2023 | Govari et al. | |
| 2023/0149070 A1 | 5/2023 | Olson et al. | |
| 2024/0099769 A1 | 3/2024 | Sharma | |
| 2024/0180613 A1 | 6/2024 | D'Agostino et al. | |
| 2024/0216052 A1 | 7/2024 | Rodriguez Soto et al. | |
| 2025/0000574 A1 | 1/2025 | Bar-Tal et al. | |
| 2025/0009404 A1 | 1/2025 | Sabban et al. | |
| 2025/0082396 A1 | 3/2025 | Bar-Tal et al. | |
| 2025/0221761 A1 | 7/2025 | Viswanathan | |
| 2025/0246316 A1 * | 7/2025 | Villongco | G16H 50/50 |

FOREIGN PATENT DOCUMENTS

| | | |
|---|---|---|
| WO | WO-2016090175 A1 | 6/2016 |
| WO | WO-2019055512 A1 | 3/2019 |
| WO | WO-2021119479 A1 | 6/2021 |
| WO | WO-2021195311 A1 | 9/2021 |
| WO | WO-2022058865 A1 | 3/2022 |
| WO | WO-2022192522 A1 | 9/2022 |
| WO | WO-2023220419 A1 | 11/2023 |
| WO | WO-2023235337 A1 | 12/2023 |
| WO | WO-2023250370 A1 | 12/2023 |
| WO | WO-2024041285 A1 | 2/2024 |
| WO | WO-2024047215 A1 | 3/2024 |
| WO | WO-2024073765 A2 | 4/2024 |
| WO | WO-2024092134 A1 | 5/2024 |
| WO | WO-2024157117 A1 | 8/2024 |

OTHER PUBLICATIONS

International Search Report and Written Opinion for International Application No. PCT/US2023/075681 dated Apr. 3, 2024, 16 pages.
International Search Report and Written Opinion for PCT Application No. PCT/US2023/068807 dated Oct. 11, 2023, 20 pages.
Invitation to pay additional fees and Partial Search Report for International Application No. PCT/US2023/075681, dated Feb. 8, 2024, 11 pages.
Invitation to pay additional fees issued in International Application No. PCT/US2024/061649, date of mailing Mar. 27, 2025, 15 pages.
International Search Report and Written Opinion for PCT Application No. PCT/US2025/023151 mailed Jul. 11, 2025, 14 pages.
International Search Report and Written Opinion for PCT Application No. PCT/US2024/061649 mailed May 20, 2025, 19 pages.
Non-Final Office Action for U.S. Appl. No. 19/094,761 mailed May 19, 2025, 8 pages.

* cited by examiner

401

403

405

APPARATUS AND METHODS FOR PULSED FIELD ABLATION INCLUDING COMPRESSIBLE ELECTRODES

CROSS-REFERENCE TO RELATED APPLICATIONS

This application is a continuation of PCT Application No. PCT/US2023/068807, filed Jun. 21, 2023, titled "APPARATUS AND METHODS FOR RENAL DENERVATION," which claims priority to and the benefit of U.S. Provisional Patent Application No. 63/354,133, filed Jun. 21, 2022, titled "APPARATUS AND METHODS FOR RENAL DENERVATION," the disclosure of each of which is incorporated by reference in its entirety.

BACKGROUND

Hypertension is a widespread condition in the modern world and while some forms of it can be controlled by means of medication, resistant hypertension is not easily controlled by drugs, as the name suggests. Given the link of hypertension to a number of disease states and hypertension's progressive nature, it is desirable to keep hypertension in check. One form of therapy that has been used to address resistant hypertension is renal denervation, where the renal nerves leading to the kidneys are ablated. This can reduce renal sympathetic nerve activity and lead to a reduction in blood pressure. While thermal modalities such as radiofrequency (RF) ablation or ablation with ultrasound have been employed in this application, they often carry the risk of collateral damage and considerable tissue necrosis in the treated areas.

Pulsed field ablation, also known as irreversible electroporation, has emerged as a potentially useful ablation modality that has been investigated in some tumor applications and has recently been found to be fruitful in the context of cardiac ablation for the treatment of cardiac arrhythmias. This non-thermal ablation modality can be tissue selective and minimize collateral damage while also resulting in a post-ablation natural healing process that preserves the extracellular matrix and overall tissue integrity. While devices and waveforms have been devised that are appropriate in the cardiac ablation context, there is a need for new devices and tools that may be more appropriate for use in the context of renal denervation ablation.

The present invention addresses the need for minimally invasive devices for the efficient and effective delivery of pulsed field ablation therapy, especially for ablation of the renal nerves for renal denervation. Pulsed field ablation procedures can be rapid while at the same time minimizing collateral tissue damage often seen in thermal-based therapies. At the same time, post-procedural healing can be relatively quick with minimal side-effects.

BRIEF DESCRIPTION

The present disclosure describes tools and devices for minimally invasive access and therapy delivery, e.g., for ablation of the renal nerves or ablation of target tissue near one or more anatomical passageways (e.g., vascular or non-vascular). The devices of the present disclosure are catheter devices introduced via standard minimal access methods and can have a distal portion with at least two sets of electrodes linearly disposed along a distal device shaft. Each set can comprise at least three electrodes. In embodiments, each set of electrodes comprises a multiplicity of solid electrodes, each with a ring-like or cylindrical geometry disposed along the shaft with an inter-electrode spacing between adjacent electrodes. The two sets of electrodes are separated by an inter-set spacing that is at least 50% greater than the inter-electrode spacing. The first set of electrodes and the second set of electrodes are wired separately with separate lead wires, e.g., first and second lead wires respectively, for electrical connection to a generator source for pulsed field ablation energy. Each lead wire is insulated with insulation capable of withstanding a voltage of at least about 300 Volts across its thickness without dielectric breakdown. In embodiments, each lead wire is insulated with insulation capable of withstanding a voltage of at least about 700 Volts across its thickness without dielectric breakdown. In embodiments, at least one of the first lead wire or the second lead wire runs through a dedicated lumen inside the catheter for that lead wire. In embodiments, the catheter shaft has a guidewire lumen that runs along its length all the way to the distal tip of the catheter; in this case, the device is an over-the-wire catheter that is introduced into at least a portion of desired anatomy over a previously introduced guidewire, with the guidewire offering mechanical support for introduction of the catheter. In embodiments, a portion of the catheter shaft is deflectable (for example, with appropriate suitably incorporated pull wires in the catheter shaft) and this deflection can be used for navigation/access to target anatomy, for example, renal vasculature.

In embodiments, the most distal electrode is separated from the distal tip of the catheter by at least about 6 mm. In embodiments, the portion of the catheter shaft that is distal to the most distal electrode is tapered with a linear or curvilinear taper where the shaft diameter progressively decreases along the distal direction. The electrodes can be made of stainless steel, Nitinol, gold, platinum-iridium alloy, or other such biocompatible materials known in the art that are suitable for delivering electric current or voltage to tissue. The electrodes are mounted on the catheter shaft, attached to suitably exposed portions of a lead wire and are swaged or crimped tightly to the shaft. In embodiments, the electrodes can be mounted on short polymer tubes that are attached to the catheter shaft using standard catheter assembly methods.

In embodiments, each electrode can comprise a cage-like structure comprising struts made at least in part from a highly elastic but compliant material such as, for example, Nitinol. The electrodes are mounted on the catheter shaft, and, in embodiments, they can be crimped securely to the shaft at one end of the electrode while the other end fits over the catheter shaft but is free to move or slide along the shaft as the cage-like structure deforms. In embodiments, the secured end of the electrode has a collar portion that makes it easier for crimping or other forms of secure attachment. When advanced into a vascular structure or other anatomical passageway whose inner diameter is smaller than the undeformed or unstressed outer diameter of the electrode, the cage-like structure can collapse (e.g., gently or with minimal force) into a configuration with a reduced diameter that fits in the vascular structure or other anatomical passageway, while at the same time elongating as the free end of the cage-like structure slides on the catheter shaft. Thus, the diameter of the electrode conforms to the vessel inner diameter over a range of vessel diameters. In embodiments, the collar of the electrode can be on the proximal end of each electrode in the distal electrode set (or a more distal electrode set) and on the distal end of each electrode in the proximal electrode set (or a more proximal electrode set).

In embodiments, there can be more than one lead wire connected to each electrode set. In the various embodiments described here, the first electrode set can be placed distally with respect to the second electrode set. For access to the renal arteries, a sheath is inserted into the femoral artery through groin access and advanced and positioned with suitable deflection to access the left or right renal artery. The sheath may have a curved or shaped distal portion with a fixed curve, or it may be a deflectable sheath. A guidewire is inserted through the sheath and advanced into the renal artery. The catheter device of the present disclosure is inserted through the sheath and over the guidewire and positioned in the appropriate renal artery.

For pulsed field ablation delivery, the first and second electrode sets can be activated with opposite electrical polarities so that a relative voltage potential difference exists between the two sets. The electric field generated thereupon is concentrated in an approximately cylindrical volume disposed between the two sets of electrodes, and targeted tissue within this volume can be ablated. Pulsed voltage waveforms suitable for such applications are disclosed in International Patent Application No. PCT/US23/25064, titled "Apparatus, Systems and Methods for Soft Tissue Ablation," filed Jun. 12, 2023, incorporated herein by reference. Pulsed field ablation application can be repeated at a given site as needed for an enhanced ablation effect before moving the catheter to a different location along the renal artery and delivering ablation at a different location. In general, multiple such sites can be targeted in each renal artery, including, for example, between 1 and about 9 such locations can be targeted in each renal artery, including all values and sub-ranges therebetween.

In embodiments where the electrodes are ring electrodes, the electrodes can range from approximately 1 mm to approximately 5 mm in outer diameter, including all values and sub-ranges therebetween. In embodiments where the electrodes comprise a cage-like structure, the outer diameter of the unstressed or undeformed configuration can lie in the range from approximately 2 mm to approximately 10 mm, including all values and sub-ranges therebetween. In embodiments where the electrodes comprise ring electrodes or a cage-like structure (when the electrodes are unstressed or undeformed), the length of each electrode can lie in the range of between approximately 0.7 mm and approximately 20 mm, including all values and sub-ranges therebetween. In embodiments, the electrodes can have unequal lengths, while maintaining approximately equal spacing between adjacent electrodes in each electrode set (e.g., first electrode set or second electrode set) in the undeformed configuration.

In embodiments, the inter-electrode spacing can range from approximately 1 mm to approximately 7 mm, including all values and sub-ranges therebetween, while the inter-set spacing can range from approximately 3 mm to approximately 15 mm, including all values and sub-ranges therebetween. In embodiments, the number of electrodes in the first set of electrodes can be in the range from 1 to about 10 including all values and sub-ranges therebetween, and likewise for the second set of electrodes.

The shaft of the catheter can range from approximately 1 mm in diameter to approximately 5 mm in diameter, including all values and sub-ranges therebetween, in various embodiments. In embodiments, the distal portion of the catheter can have a taper such that the distal tip of the catheter has an outer diameter that is less than the diameter of a more proximal portion of the shaft by at least about 0.5 mm. In embodiments, the voltage associated with pulsed field ablation delivery can range from approximately 700 Volts to approximately 10,000 Volts, including all values and sub-ranges therebetween.

In some embodiments, an apparatus includes: a shaft including a distal flexible portion; a first set of electrodes disposed on the distal flexible portion, the first set of electrodes including at least three electrodes that are spaced from one another by a first set of inter-electrode spacings, the first set of electrodes being jointly wired to one another via a first lead wire; and a second set of electrodes disposed on the distal flexible portion distal to the first set of electrodes, the second set of electrodes including at least three electrodes that are spaced from one another by a second set of inter-electrode spacings, the second set of electrodes being jointly wired to one another via a second lead wire, the second set of electrodes being spaced from the first set of electrodes by an inter-set spacing, the inter-set spacing being at least 50% greater than each inter-electrode spacing of the first and second sets of inter-electrode spacings, the first and second sets of electrodes configured to deliver pulsed field ablation.

In some embodiments, an apparatus includes: a shaft including a distal flexible portion; a first set of electrodes disposed on the distal flexible portion, the first set of electrodes including at least one basket electrode that is formed of a superelastic material and has a diameter greater than a diameter of the shaft in an unstressed configuration, the first set of electrodes being spaced from one another by a first set of inter-electrode spacings, the first set of electrodes being jointly wired to one another via a first lead wire; and a second set of electrodes disposed on the distal flexible portion distal to the first set of electrodes, the second set of electrodes being spaced from one another by a second set of inter-electrode spacings, the second set of electrodes being jointly wired to one another via a second lead wire, the second set of electrodes being spaced from the first set of electrodes by an inter-set spacing, the inter-set spacing being at least 50% greater than each inter-electrode spacing of the first and second sets of inter-electrode spacings, the first and second sets of electrodes configured to deliver pulsed field ablation.

In some embodiments, a method includes: positioning a distal flexible portion of a catheter in a first section of anatomy (e.g., vascular or non-vascular), the distal flexible portion having first and second sets of electrodes disposed thereon, each of the first and second sets of electrodes (1) including at least three electrodes with inter-electrode spacing between adjacent electrodes and (2) being separated from one another by an inter-set spacing that is at least 50% larger than each inter-electrode spacing; delivering high voltage pulses to the first and second electrode sets to ablate the first section of the anatomy; moving the distal flexible portion of the catheter to a second section of the anatomy; and delivering high voltage pulses to the first and second electrode sets to ablate the second section of the anatomy.

In some embodiments, an apparatus includes: a shaft including a distal flexible portion; and a plurality of electrodes disposed on the distal flexible portion, the plurality of electrodes being wired to one or more lead wires and being configured to deliver pulsed field ablation, the plurality of electrodes including at least one basket electrode that is formed of a superelastic material, the basket electrode being configured to transition from an unstressed configuration to a stressed configuration by being compressed, the basket electrode in the unstressed configuration having a diameter greater than a diameter of the shaft, the basket electrode including: a collar portion that is attached to the shaft and to one of the one or more lead wires; and an open end opposite the collar portion that is configured to move or slide on the shaft as the basket electrode is compressed into the stressed configuration.

In some embodiments, an apparatus includes: a catheter device including a distal portion; a first set of one or more electrodes disposed on the distal portion, the first set of electrodes being spaced from one another by a first set of inter-electrode spacings, the first set of electrodes being jointly wired to one another via a first lead wire; and a second set of one or more electrodes disposed on the distal portion distal to the first set of electrodes, the second set of electrodes being spaced from one another by a second set of inter-electrode spacings, the second set of electrodes being jointly wired to one another via a second lead wire, the first set of electrodes and the second set of electrodes including at least one basket electrode that is formed of a superelastic material and is configured to be compressed, the basket electrode including: a fixed end that is attached to the distal portion and to a respective one of the first and second lead wires; and an open end opposite the fixed end that is configured to move or slide on the distal portion as the basket electrode is compressed, the first and second sets of electrodes configured to deliver pulsed field ablation.

In some embodiments, an apparatus includes: a catheter device including a distal portion; a first electrode disposed on the distal portion, the first electrode being coupled to a first lead wire; and a second electrode disposed on the distal portion distal to the first electrode, the second electrode being coupled a second lead wire, the first and second electrodes including at least one basket electrode that is formed of a superelastic material and is configured to be compressed, the basket electrode including: a fixed end that is attached to the distal portion and to a respective one of the first and second lead wires; and an open end opposite the fixed end that is configured to move or slide on the distal portion as the basket electrode is compressed, the first and second sets of electrodes configured to deliver pulsed field ablation.

In some embodiments, a method includes: positioning a distal flexible portion of a catheter device in a first section of anatomy, the distal flexible portion having first and second sets of electrodes disposed thereon, at least the first set of electrodes or the second set of electrodes including at least one basket electrode that is formed of a superelastic material, the basket electrode including a fixed end that is attached to the distal flexible portion and an open end opposite the fixed end that is configured to move or slide on the distal flexible portion such that the basket electrode can be compressed based on a dimension of the anatomy in which the basket electrode is disposed; delivering high voltage pulses to the first and second electrode sets to ablate the first section of the anatomy; moving the distal flexible portion of the catheter to a second section of the anatomy; and delivering high voltage pulses to the first and second electrode sets to ablate the second section of the anatomy.

DETAILED DESCRIPTION

The device embodiments of the present disclosure provide device constructions and configurations for the delivery of irreversible electroporation or pulsed field ablation therapy, e.g., for renal denervation where the renal nerves are ablated for the treatment of resistant hypertension. In embodiments, the devices are intended for minimally invasive use and may be intended for use as an over-the-wire device where the device is tracked over a guidewire for placement in the renal arteries, while in other embodiments, they can be deflectable devices for navigation and placement.

Figure 1:
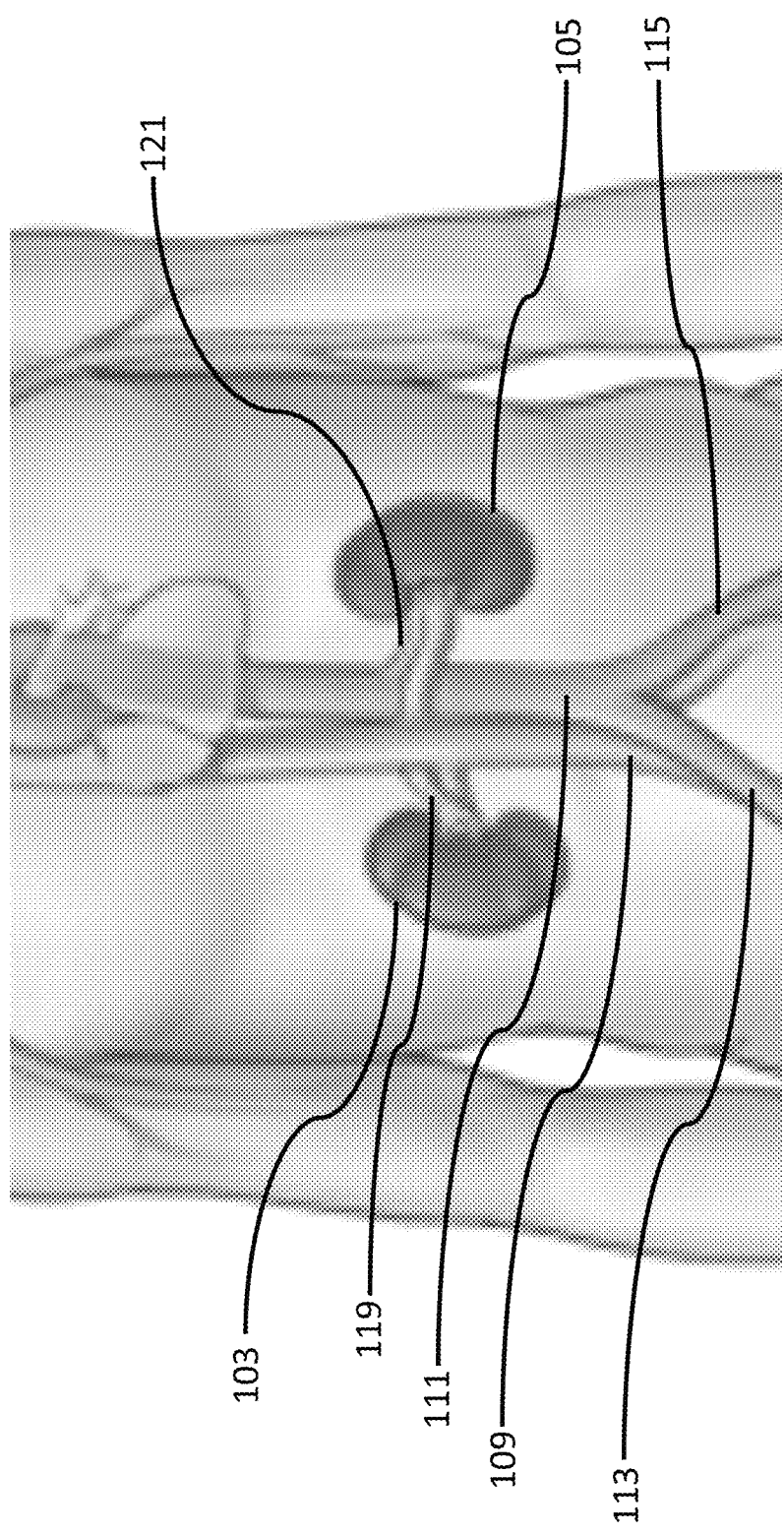
FIG. 1 is a schematic illustration of a subject anatomy indicating the kidneys, renal arteries and associated access vasculature.

For the placement of the device in the left or right renal artery, the device can initially be introduced in the left or right femoral artery via standard groin access. For context, FIG. 1 shows the anatomy of the femoral and renal arteries and the kidneys. The left and right femoral arteries (respectively 115 and 113) branch off from the lower portion of the descending aorta 111, which runs alongside the inferior vena cava 109. The left renal artery 121 and the right renal artery 119 branch off from the descending aorta and respectively run to the left kidney 105 and the right kidney 103.

Figure 2:
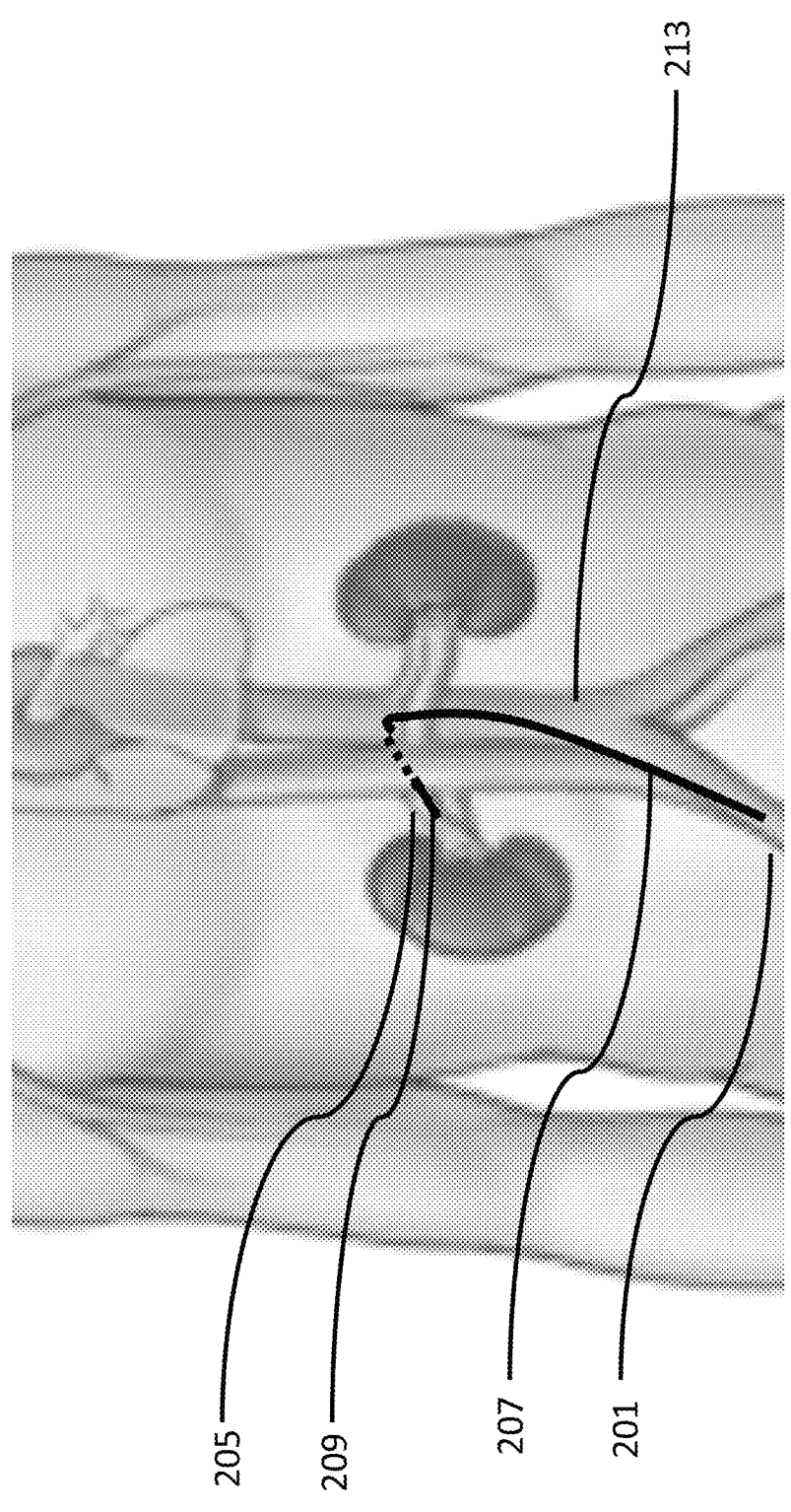
FIG. 2 provides an illustration of a subject anatomy including renal arteries with a device access path highlighted, according to embodiments.

As shown in the example in FIG. 2, the catheter device 207 is introduced via groin access into the right femoral artery 201 and thence via the descending aorta 213, it is introduced into the right renal artery 205, as indicated by the distal portion of the device 209 positioned in the right renal artery. In embodiments, the catheter device may be passed through a guidewire inside a sheath (separate devices are not shown in the schematic in FIG. 2). With the distal portion of the sheath suitably deflected and positioned so as to gain access to the renal artery, the guidewire is extended into the renal artery and the catheter can be tracked over the guidewire and positioned in the renal artery under fluoroscopic visualization or other suitable types of visualization. The electrodes on the catheter can be visualized on a X-ray image. In embodiments, the electrodes, or portions of the shaft under or near the electrodes, can be "doped" with additional materials (e.g., such as tungsten) for enhanced visualization on X-ray images. In embodiments, the catheter device can be deflectable via a standard mechanism such as, for example, one or more pull wires, and the catheter navigated and positioned in the renal artery without a guidewire.

Figure 3A:
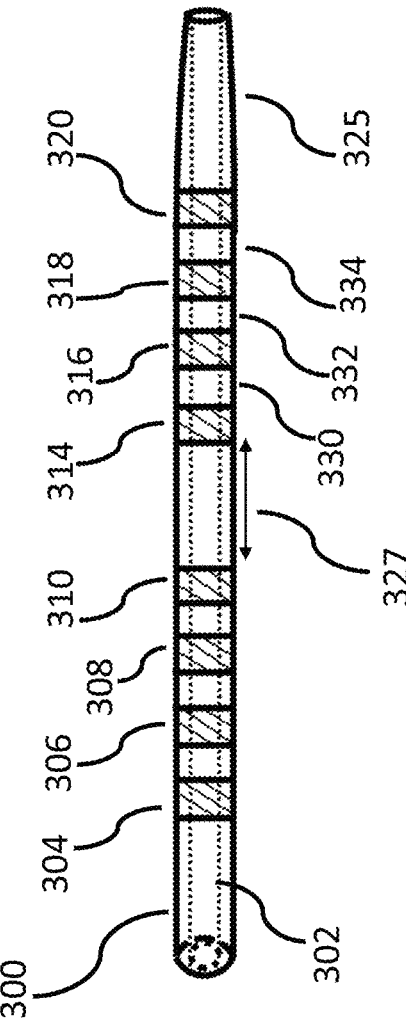
FIG. 3A is a schematic illustration of a device embodiment showing a first set of electrodes and a second set of electrodes with a spacing between the first and second electrode sets.

FIG. 3A is a schematic illustration of a device embodiment with ring-like electrodes showing a first set of electrodes and a second set of electrodes with a spacing between the first and second electrode sets. Each set of electrodes can comprise one, at least two, or at least three electrodes. Catheter 300 is shown having a guidewire lumen 302 running along the length of the catheter to its distal tip. In the example in this figure, a first set of electrodes 314, 316, 318 and 320 is shown along with a second set of electrodes 304, 306, 308 and 310, and with an inter-set spacing 327 separating the first and second sets of electrodes. In some embodiments, the total length of the first set of electrodes, measured from the proximal end of the most proximal electrode of the first set of electrodes to the distal end of the most distal electrode of the first set of electrodes, is at least about three times larger than the catheter shaft diameter. Likewise, in some embodiments, the total length of the second set of electrodes, measured from the proximal end of the most proximal electrode of the second set of electrodes to the distal end of the most distal electrode of the second set of electrodes, is at least about three times larger than the catheter shaft diameter. In the first set of electrodes, inter-electrode spacing 330 (i.e., the spacing between nearest edges of adjacent electrodes in a set of electrodes) separates electrodes 314 and 316, inter-electrode spacing 332 separates electrodes 316 and 318, and inter-electrode spacing 334 separates electrodes 318 and 320. Likewise, there are inter-electrode spacings in the second set of electrodes. In embodiments, the inter-electrode spacings can be approximately equal, while in other embodiments, they can differ from each other. In either case, the inter-set spacing 327 is at least 50% larger than any of the inter-electrode spacings. In embodiments, the distal edge of the most distal electrode is separated from the distal tip of the catheter 300 by at least about 6 mm. In embodiments, the portion of the catheter shaft that is distal to the most distal electrode 320 is tapered in a linear or curvilinear taper 325, where the shaft diameter progressively decreases along the distal direction.

In embodiments, the first set of electrodes and the second set of electrodes are wired separately with separate lead wires, e.g., first and second lead wires respectively, for electrical connection to a generator source for pulsed field ablation energy. Each lead wire is insulated with insulation capable of withstanding a voltage of at least about 300 Volts across its thickness without dielectric breakdown. In embodiments, each lead wire is insulated with insulation capable of withstanding a voltage of at least about 700 Volts across its thickness without dielectric breakdown. In embodiments where the catheter shaft has a guidewire lumen that runs along its length all the way to the distal tip of the catheter, the catheter can be an over-the-wire catheter that is introduced into at least a portion of desired vasculature or other anatomy over a previously introduced guidewire, with the guidewire offering mechanical support for introduction of the catheter. In embodiments, a portion of the catheter shaft is deflectable (for example, with appropriate suitably incorporated pull wires in the catheter shaft) and this deflection can be used for navigation and/or access to the renal vasculature or other target anatomy.

In embodiments, the electrodes can be made of stainless steel, Nitinol, gold, platinum-iridium alloy, or other such biocompatible materials known in the art that are suitable for delivering electric current or voltage to tissue. The electrodes are mounted on the catheter shaft, attached to suitably exposed portions of a lead wire and are swaged or crimped tightly to the shaft. In embodiments, the electrodes can be mounted on short polymer tubes that are attached to the catheter shaft using standard catheter assembly methods.

Figure 3B:
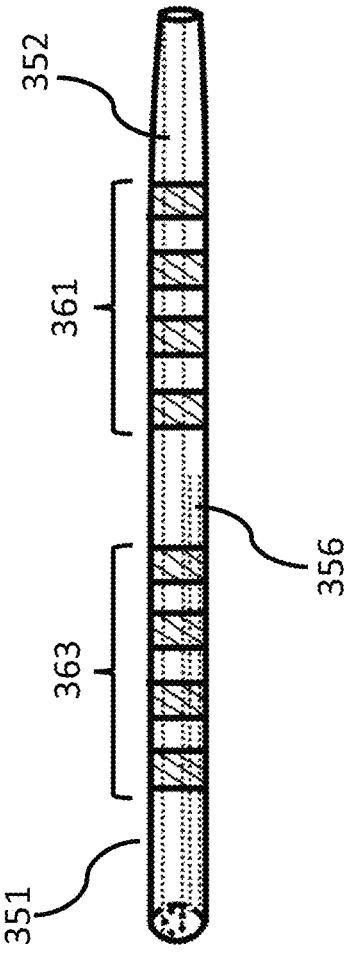
FIG. 3B is a schematic illustration of a device embodiment showing a first set of electrodes and a second set of electrodes with a spacing between the first and second electrode sets and with a separate lumen for at least one electrical lead for connection to the first set of electrodes.

In embodiments, at least one of the first lead wire or the second lead wire runs through a dedicated lumen inside the catheter for that lead wire. FIG. 3B schematically illustrates a device embodiment 351 showing a first set of electrodes 361 and a second set of electrodes 363 with a spacing between the first and second electrode sets, with a dedicated guidewire lumen 352, and with a separate lumen 356 that terminates at a location between the first and second electrode sets. The separate lumen 356 is a dedicated lumen for the passage of one or more electrical leads that connect to the first set of electrodes 361. The lumen 356 can terminate in an open space wherein one or more lead wire(s) with insulation removed in part can connect to the electrodes of the first set of electrodes 361. The lumen 356 can be made of polymeric material that provides an additional layer of electrical insulation between the lead wires in the lumen and any exposed lead wires outside the lumen 356, including, for example, the lead wires that connect to the second set of electrodes 363. In some embodiments, the polymeric material defining or forming the lumen 356 can be capable of withstanding a voltage of at least about 300 Volts across its thickness without dielectric breakdown.

In the case of ring electrodes embodiments as described above, the electrodes of the present disclosure can range from approximately 1 mm to approximately 5 mm in outer diameter, including all values and sub-ranges therebetween. In such embodiments, the length of each electrode can lie in the range of between approximately 0.7 mm and approximately 20 mm, including all values and sub-ranges therebetween. In embodiments, the electrodes can have unequal lengths, while maintaining approximately equal spacing between adjacent electrodes in each electrode set (e.g., first electrode set or second electrode set). The inter-electrode spacing can range from approximately 1 mm to approximately 7 mm, including all values and sub-ranges therebetween, while the inter-set spacing can range from approximately 3 mm to approximately 15 mm, including all values and sub-ranges therebetween. In embodiments, the number of electrodes in the first set of electrodes can be in the range from 1 to about 10, including all values therebetween, and likewise for the second set of electrodes.

Figure 4:
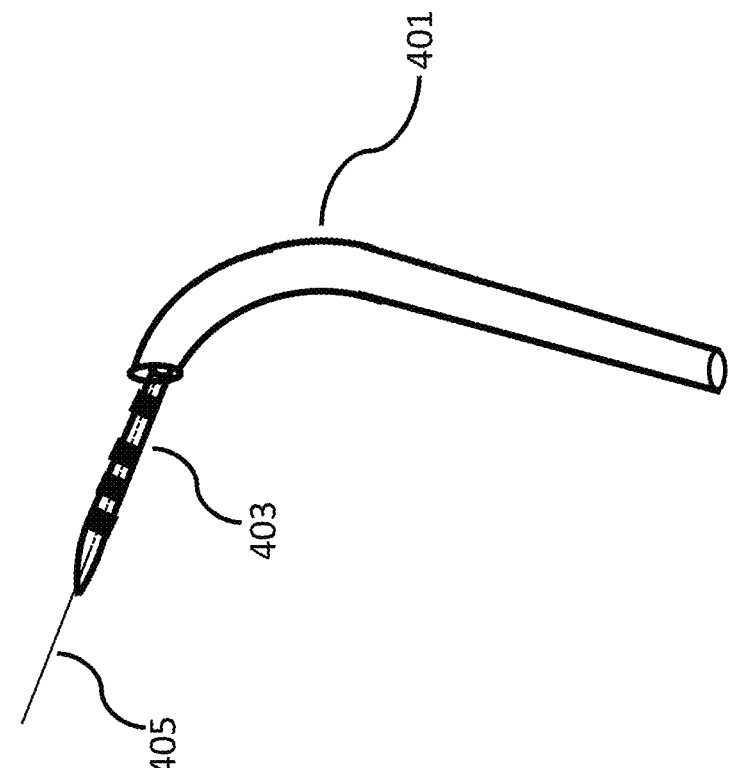
FIG. 4 illustrates a catheter device of the present disclosure inserted over a guidewire and with the catheter device and guidewire inserted into a sheath with a curved distal portion, according to embodiments.

FIG. 4 illustrates a catheter device 403 of the present disclosure inserted over a guidewire 405 and with the catheter device and guidewire inserted into a sheath 401 with a curved distal portion, according to embodiments. The sheath 401 can be a deflectable sheath or it can be a fixed curve sheath. In use, the sheath 401 can be positioned at or near the entrance to a renal artery with a suitable deflection for access to the renal artery, e.g., as visualized under fluoroscopic guidance. The guidewire 405 is extended into the renal artery and offers support for tracking the catheter 403 over the guidewire and positioning the catheter 403 in the renal artery.

Figure 5:
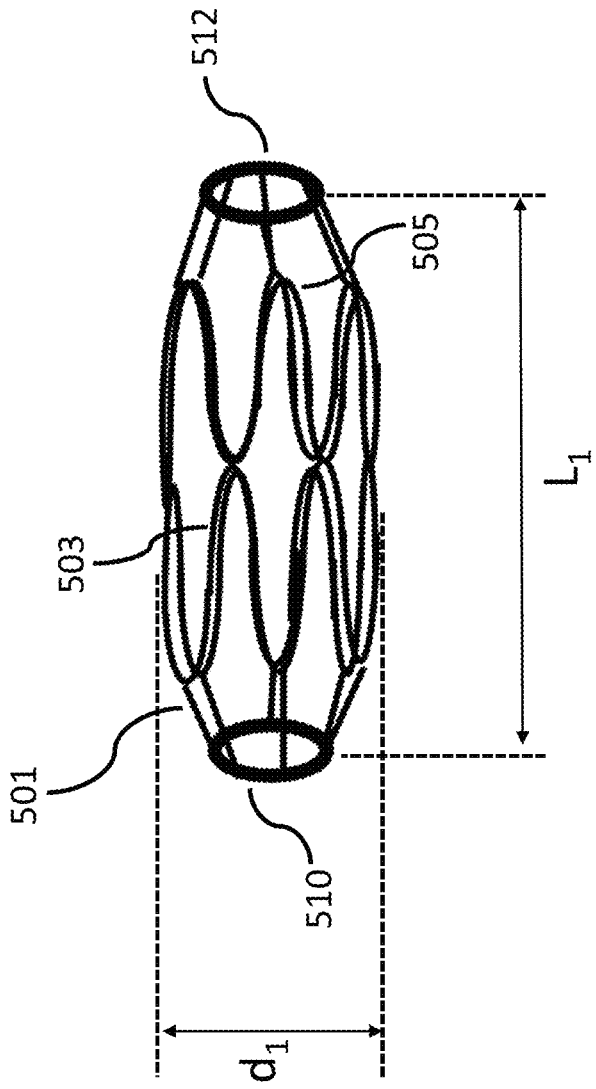
FIG. 5 is a schematic illustration of an unstressed or undeformed configuration of an electrode with a cage-like structure comprising struts or substantially similar structure, with the electrode being part of a catheter device of the present disclosure and located on the catheter device shaft, according to embodiments.

FIG. 5 is a schematic illustration of an unstressed or undeformed configuration of an electrode 501 with a cage-like structure comprising a multiplicity of struts (or substantially similar structure) such as 503 and 505, and with ends 510 and 512. In embodiments, the electrode 501 can be or form part of a catheter device of the present disclosure (e.g., catheter device 207) and be located on the catheter device shaft. The struts of the cage-like structure comprise a superelastic or hyperelastic material (e.g., such as Nitinol) that is compliant and can deform under application of mechanical stress, while being able to rapidly return to their unstressed configuration as the mechanical stress is released. In the unstressed configuration, the electrode 501 has a length L1 between its ends 510 and 512 and a diameter d1 at its widest portion, as shown in FIG. 5. These parameters can change when the electrode 501 is stressed and transitions from its unstressed configuration to a stressed configuration.

Figure 6:
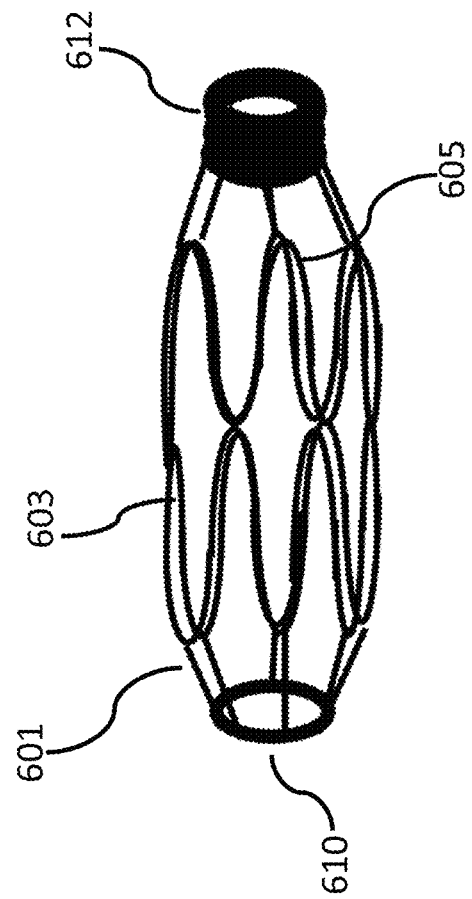
FIG. 6 is a schematic illustration of an unstressed or undeformed configuration of an electrode with a cage-like structure comprising struts or substantially similar structure and a collar portion at one end, with the electrode being part of a catheter device of the present disclosure and located on the catheter device shaft, according to embodiments.
Figure 7:
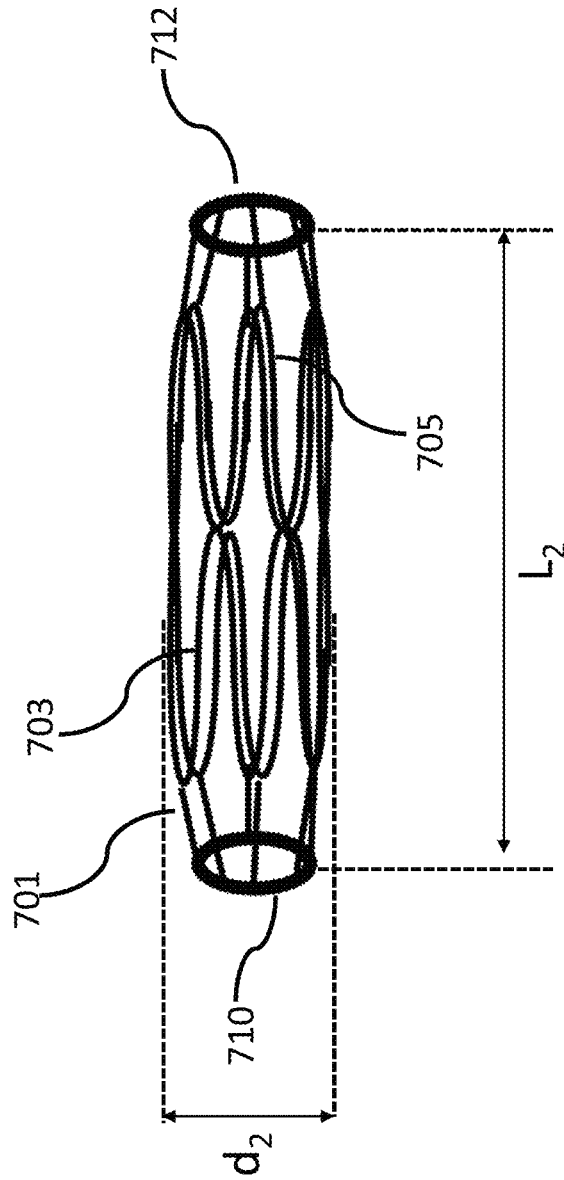
FIG. 7 is a schematic illustration of a stressed or deformed configuration of an electrode with a cage-like structure comprising struts or substantially similar structure, with the electrode being part of a catheter device of the present disclosure and located on the catheter device shaft, according to embodiments.

In embodiments, as illustrated in FIG. 6, an electrode 601 comprises a cage-like structure comprising a multiplicity of struts (or substantially similar structure) such as for example 603 and 605 and can include a collar portion 612 at one end, where the collar portion 612 is a ring or ring-like extension. The collar portion 612 can be used to fix the electrode 601 to the shaft of a catheter device, e.g., by crimping, swaging or other means of attachment, and for connection of a lead wire to the underside of the collar portion 612 and thus to the electrode 601. Therefore, the electrode can include a fixed end. When the electrode 601 is mounted on a catheter shaft, the other end 610 of the electrode 601 (e.g., the end opposite of the collar portion 612 or open end) can be free to move or slide on the catheter shaft as the electrode is compressed, thus, allowing the cage-like structure of the electrode 601 to change to a stressed or deformed configuration. Such a stressed configuration is illustrated in FIG. 7, which is a schematic illustration of a stressed or deformed configuration of an electrode 701 with a cage-like structure comprising a multiplicity of struts (or substantially similar structure) such as for example 703 and 705, and with ends 710 and 712. In embodiments, the electrode can comprise part of a catheter device of the present disclosure and be located on the catheter device shaft. While FIG. 7 does not show a collar on one end as in FIG. 6, it can be appreciated that in embodiments, the cage-like structure can include a collar on one end. In the stressed or deformed configuration indicated in FIG. 7, the electrode 701 has a length L2 between its ends 710 and 712 and diameter d2 at its widest portion. In comparison to the unstressed configuration, e.g., as shown in FIG. 5, the length L2 and diameter d2 in the stressed configuration in FIG. 7 are different from their respective unstressed values L1 and d1. Specifically, when the electrode is radially compressed, the stressed length and diameter respectively have values such that $L2 > L1$ and $d2 < d1$. These comparative relationships between the stressed and unstressed electrode configurations hold in electrode embodiments without a collar (e.g., as shown in FIGS. 5 and 7) as well as in embodiments that include a collar (e.g., as shown in FIG. 6).

Figure 8:
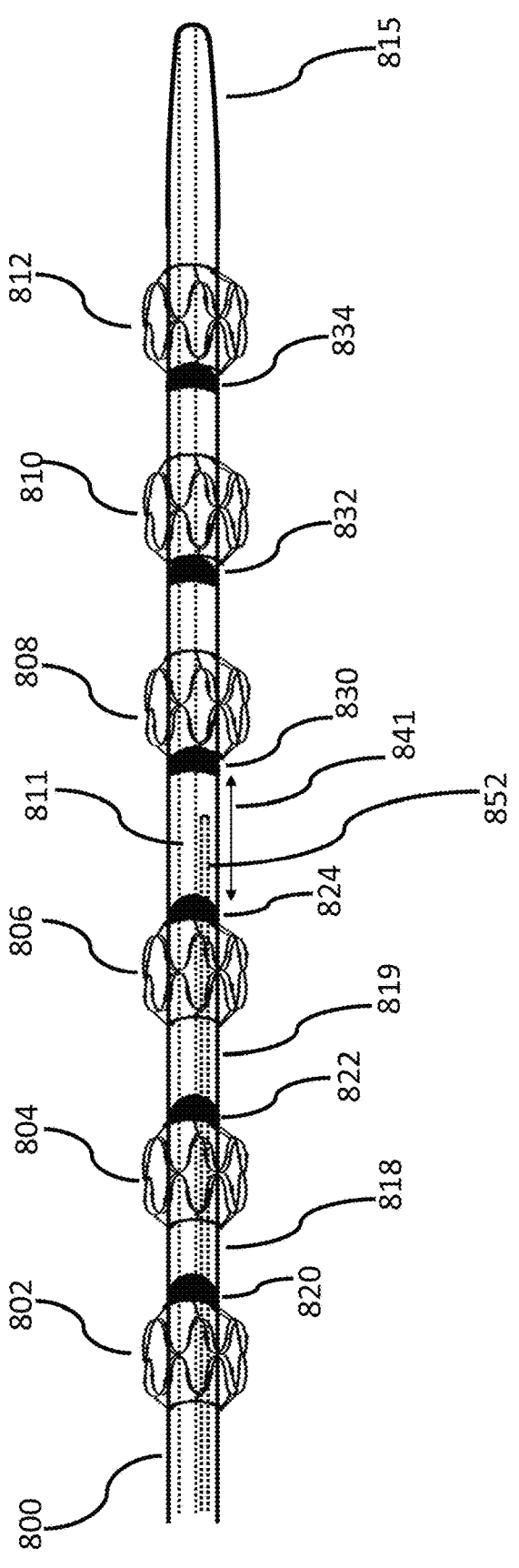
FIG. 8 is a schematic illustration of a device embodiment showing a first set of electrodes and a second set of electrodes with a spacing between the first and second electrode sets, with each electrode shown in an unstressed or undeformed configuration and comprising a cage-like structure comprising struts or substantially similar structure, and with a separate lumen for at least one electrical lead for connection to the first set of electrodes.

FIG. 8 is a schematic illustration of a device embodiment in the form of a catheter 800 showing a first set of electrodes 808, 810 and 812 and a second set of electrodes 802, 804 and 806, with an inter-set spacing 841 between the first and second electrode sets, with each electrode comprising a cage-like structure comprising struts (or substantially similar structure) as shown in an unstressed or undeformed configuration, and with a separate lumen 852 for at least one electrical lead for connection to the first set of electrodes. Each set of electrodes can comprise one, at least two, or at least three electrodes. In embodiments, the catheter 800 also includes a guidewire lumen 811 running along the length of the catheter to its distal tip. Electrodes 808, 810 and 812 of the first electrode set respectively have collar portions 830, 832 and 834, while electrodes 802, 804 and 806 of the second electrode set respectively have collar portions 820, 822 and 824. In some embodiments, the total length of the first set of electrodes, measured from the proximal end of the most proximal electrode of the first set of electrodes to the distal end of the most distal electrode of the first set of electrodes, is at least about three times larger than the catheter shaft diameter. Likewise, in some embodiments, the total length of the second set of electrodes, measured from the proximal end of the most proximal electrode of the second set of electrodes to the distal end of the most distal electrode of the second set of electrodes, is at least about three times larger than the catheter shaft diameter. Adjacent electrodes of each electrode set are separated by inter-electrode spacings. For example, inter-electrode spacing 818 separates electrodes 802 and 804 while inter-electrode spacing 819 separates electrodes 804 and 806. While the collars are fixed to the shaft, the other end of each electrode (e.g., the end without a collar) is free to slide along the catheter shaft. Thus, the inter-electrode spacings such as 818 and 819 can vary depending on the deformation of the corresponding electrodes 804 and 806, respectively. In the embodiment shown in FIG. 8, the collars 824 and 830 abut the inter-set spacing 841 and since the collars are fixed, the inter-set spacing 841 is fixed, although the inter-electrode spacings can vary depending on the deformation of the electrodes. In embodiments, the inter-set spacing 841 is at least 50% larger than the largest inter-electrode spacing, including over the entire range of variation of the latter (e.g., as caused by the deformation of the electrodes). In other embodiments, the collars can be placed oppositely compared to the illustration in FIG. 8 (i.e., the electrode ends abutting the inter-set spacing 841 can be without collars), in which case the inter-set spacing can vary. In this case, the smallest value of inter-set spacing 841 (e.g., when the electrodes 806 and 808 are deformed) is at least 50% larger than the largest inter-electrode spacing over the entire range of variation of the latter.

In embodiments, the inter-electrode spacings (e.g., in the case of cage-like electrodes, when the electrodes are undeformed or unstressed) can be approximately equal, while in other embodiments they can differ from each other. In either case, the inter-set spacing 841 is at least 50% larger than any of the inter-electrode spacings. In embodiments, the distal edge of the most distal electrode is separated from the distal tip of the catheter by at least about 6 mm. In embodiments, the portion of the catheter shaft that is distal to the most distal electrode is tapered in a linear or curvilinear taper 815, where the catheter shaft diameter progressively decreases along the distal direction.

In embodiments, the electrodes when unstressed or unde-formed can have unequal lengths, while maintaining approximately equal spacing between adjacent electrodes in each electrode set (e.g., first electrode set or second elec-trode set).

In embodiments, the first set of electrodes and the second set of electrodes are wired separately with separate lead wires, e.g., first and second lead wires respectively, for electrical connection to a generator source for pulsed field ablation energy. Each lead wire is insulated with insulation capable of withstanding a voltage of at least about 300 Volts across its thickness without dielectric breakdown. In embodiments, each lead wire is insulated with insulation capable of withstanding a voltage of at least about 700 Volts across its thickness without dielectric breakdown. In embodiments where the catheter shaft has a guidewire lumen that runs along its length all the way to the distal tip of the catheter, the device is an over-the-wire catheter that is introduced into at least a portion of desired vasculature or other anatomy over a previously introduced guidewire, with the guidewire offering mechanical support for introduction of the catheter. In embodiments, a portion of the catheter shaft is deflectable (for example, with appropriate suitably incorporated pull wire(s) in the catheter shaft) and this deflection can be used for navigation/access to the renal vasculature or other target anatomy.

In embodiments, the electrodes comprising a cage-like structure can be made of a superelastic or hyperelastic or shape memory electrically conducting material such as, for example, Nitinol, with the material also being a biocompat-ible material known in the art that is suitable for delivering electric current or voltage to tissue. In embodiments, the electrodes are mounted on the catheter shaft, attached to suitably exposed portions of a lead wire and are swaged or crimped tightly to the shaft at one end. In embodiments, the electrodes can be mounted on short polymer tubes that are attached to the catheter shaft using standard catheter assem-bly methods. In embodiments, at least one of the first lead wire or the second lead wire runs through a dedicated lumen inside the catheter for that lead wire. For example, in the embodiment shown in FIG. 8, the separate lumen 852 is a dedicated lumen for one or more electrical leads with the lumen 852 terminating at a location between the first and second electrode sets. The separate lumen 852 is a dedicated lumen for the passage of one or more electrical leads that connect to the first set of electrodes 808, 810 or 812. The lumen terminates in an open space wherein the lead wire(s) with insulation removed in part can connect to the electrodes of the first set of electrodes. The lumen 852 can be made of polymeric material that provides an additional layer of electrical insulation between the lead wires in the lumen and any exposed lead wires outside the lumen 852 (e.g., includ-ing lead wires that connect to the second set of electrodes 802, 804 and 806), with the polymeric material capable of withstanding a voltage of at least about 300 Volts across its thickness without dielectric breakdown.

Figure 9:
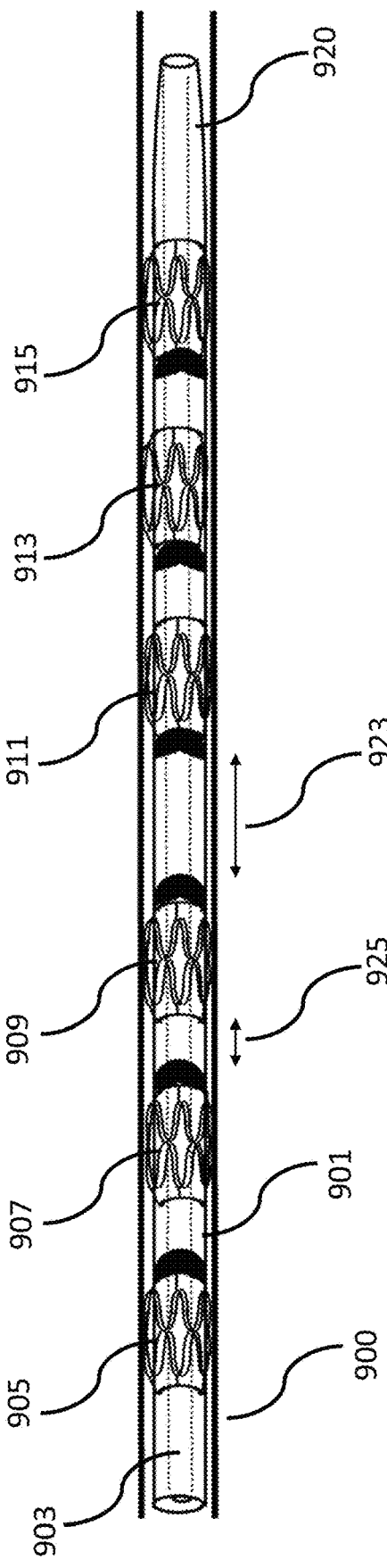
FIG. 9 shows a schematic illustration of an embodiment of a catheter device inserted into a blood vessel, showing a first set of electrodes and a second set of electrodes with a spacing between the first and second electrode sets, with each electrode shown in a stressed or deformed configuration as the catheter fits into the blood vessel, and with each electrode comprising a cage-like structure comprising struts or substantially similar structure.

FIG. 9 shows a schematic illustration of an embodiment of a catheter device 901 inserted into a blood vessel 900, showing a first set of electrodes 911, 913 and 915 and a second set of electrodes 905, 907 and 909 with an inter-set spacing 923 between the first and second electrode sets, and with each electrode comprising a cage-like structure com-prising struts (or substantially similar structure), and with each electrode shown in a stressed or deformed configura-tion as the catheter device 901 is disposed in the blood vessel 900. Inter-electrode spacings such as 925 separate the near-est edges of adjacent electrodes in each electrode set. In embodiments, the catheter device also includes a guidewire lumen 903 running along the length of the catheter to its distal tip. While FIG. 9 is intended to show the same device as in FIG. 8, in FIG. 9 the device (and specifically, the electrodes) is constrained to fit in the blood vessel 900, and accordingly the electrode configurations in FIG. 9 are stressed or deformed as compared to their respective coun-terparts in FIG. 8. In particular, the respective electrode diameters (at their respective widest value) are smaller in FIG. 9 as compared to FIG. 8, and the inter-electrode spacings such as 925 are also smaller relative to their respective counterparts in FIG. 8, since the free ends of the electrodes move to compensate mechanically for electrode compression. Since the blood vessel 900 can vary in diam-eter along its length, it can be appreciated that the electrode diameters and inter-electrode spacings 925 can be different across adjacent electrodes in each electrode set, e.g., depending on the shape or diameter of the immediate portions of the blood vessel 900 near the adjacent electrodes and how those portions would compress or deform the electrodes. For example, as the portion of the catheter shaft that is distal to the most distal electrode (shown tapered in a linear or curvilinear taper 920 where the shaft diameter progressively decreases along the distal direction) is inserted further into an artery or vessel with decreasing diameter along the path of advancement, the leading electrodes in the first electrode set can in some cases become more com-pressed or deformed as compared to the second electrode set. Nevertheless, the comparative relationships stated herein, e.g., the smallest value of inter-set spacing being at least 50% larger than the largest inter-electrode spacing (over the entire range of variation of the latter), continue to hold.

In the embodiments where the electrodes comprise a cage-like structure, the outer diameter of the unstressed or undeformed configuration can lie in the range from approxi-mately 2 mm to approximately 10 mm, including all values and sub-ranges therebetween. In such embodiments, the length of each electrode can lie in the range between approximately 0.7 mm and approximately 20 mm, including all values and sub-ranges therebetween. In embodiments, the electrodes can have unequal lengths, while maintaining approximately equal spacing between adjacent electrodes in each electrode set (e.g., first electrode set or second elec-trode set) in the undeformed configuration.

Across the range of configurations or deformations of the cage-like structure of the electrodes disclosed herein, the inter-electrode spacing can range from approximately 1 mm to approximately 7 mm, including all values and sub-ranges therebetween, while the inter-set spacing can range from approximately 3 mm to approximately 15 mm, including all values and sub-ranges therebetween. In embodiments, the number of electrodes in the first set of electrodes can be in the range from 1 to about 10 including all values and sub-ranges therebetween, and likewise for the second set of electrodes.

Figure 10:
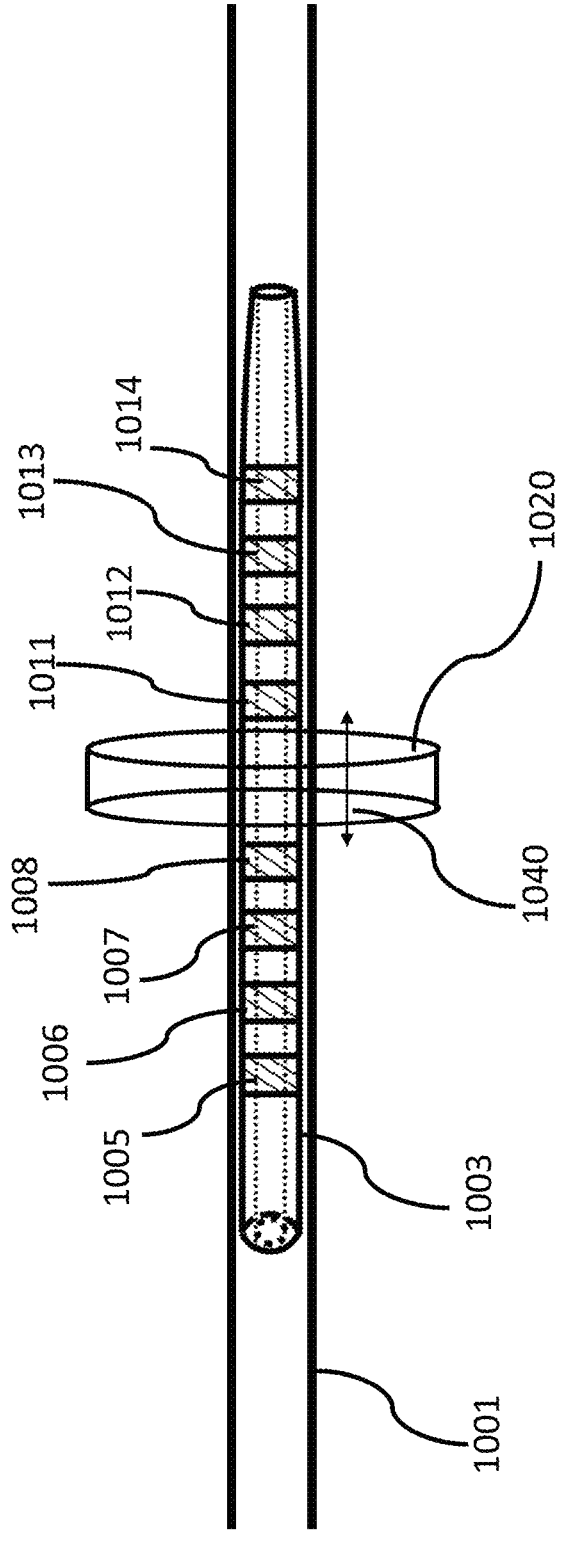
FIG. 10 is a schematic illustration of a device embodiment showing a first set of electrodes and a second set of electrodes with a spacing between the first and second electrode sets, and with a schematic indication of an ablation zone that is generated when the first and second sets of electrodes are energized with opposing electrical polarities upon delivery of a pulsed field ablation waveform.

For pulsed field ablation delivery, the first electrode set and the second electrode set can be energized with opposing electrical polarities, which results in the generation of an electric field suitable for achieving irreversible electroporation in a volume surrounding the portion of the catheter at inter-set spacing. FIG. 10 is a schematic illustration of a catheter device 1003 in an embodiment with ring electrodes placed in a blood vessel 1001, showing a first set of electrodes 1011, 1012, 1013 and 1014, and a second set of electrodes 1005, 1006, 1007 and 1008, with an inter-set spacing 1040 between the first and second electrode sets, and with a schematic indication of an ablation zone 1020 that is generated when the first and second sets of electrodes are energized with opposing electrical polarities upon delivery of a pulsed field ablation waveform. For example, when the device is placed at a location in a renal artery and pulsed field ablation is delivered, renal nerves within the ablation zone 1020 are ablated. When the pulsed field ablation waveform is applied, the spatial distribution of the resulting electric field determines the zone of ablation or cell death.

In embodiments, multiple pulsed field ablation deliveries can be performed at a given location for enhanced ablation effect. Subsequently, when the device is moved to a different location along the renal artery and pulsed field ablation is delivered, renal nerves within a similar new approximately cylindrical ablation zone are ablated. In general, multiple such sites can be targeted in each renal artery, including, for example, between 1 and about 9 such locations can be targeted in each renal artery.

The shaft of the catheter can range from approximately 1 mm in diameter to approximately 5 mm in diameter, depending on the embodiment. In embodiments, the distal portion of the catheter can have a taper such that the distal tip of the catheter has an outer diameter that is less than the shaft diameter of a more proximal portion of the catheter by at least about 0.5 mm. In embodiments, the voltage associated with pulsed field ablation delivery can range from approximately 700 Volts to approximately 10,000 Volts, including all values and sub-ranges therebetween. Variant embodiments as disclosed herein can be in the form of a deflectable catheter with deflection of the device controlled from a control mechanism, e.g., in the handle, and using mechanisms such as the use of pull wires familiar to those skilled in the art of interventional catheters.

In operation, a catheter or device such as those described herein (e.g., catheter 300, 351, 800, 901, 1003) can be advanced within a sheath (e.g., sheath 401) that is disposed within vascular anatomy or another anatomical passageway. In some embodiments, the catheter can be advanced together with a guidewire, with the guidewire extending out of the catheter lumen. The catheter can be advanced until a distal end of the catheter extends distally from a distal end of the sheath. In some embodiments, the guidewire can be extended further, and the catheter can be advanced further over the guidewire. The catheter can be advanced until it is positioned at a target site for delivering pulsed field ablation. In some embodiments, where the catheter includes one or more basket electrodes, the basket electrodes can automatically expand as the catheter is extended outside of the sheath. As described above, the basket electrodes can have a predefined diameter in an unstressed configuration. When the basket electrodes are within the sheath, the basket electrodes can have a diameter that is smaller than or substantially equal to an inner diameter of the sheath. Then when the basket electrodes are extended outside of the sheath, the basket electrodes can automatically expand to the diameter of their unstressed configuration or an inner diameter of a vessel, if the basket electrodes are disposed in a vessel having an inner diameter that is smaller than the unstressed basket electrode diameter. Stated differently, when the basket electrodes are disposed in a vessel having a size smaller than the unstressed configuration of the basket electrodes, then the basket electrodes may only partially expand within the vessel. In many instances, vessel diameter may decrease or become narrower in a distal direction, so as the catheter is advanced, any basket electrodes disposed on the catheter can compress based on the changing inner diameter of the vessel. In some instances, the catheter may start distally in a vessel and ablate at multiple locations along the vessel after the catheter is retracted in steps. In such instances, the basket electrodes can start in a more compressed configuration in the vessel and then expand gradually as the catheter is retracted or withdrawn, e.g., to the diameter of its unstressed configuration or to a partially expanded diameter based on vessel anatomy.

While systems and devices described herein are described with reference to renal denervation, it can be appreciated that systems and devices described herein can be used in other indications (e.g., for targeting different tissue and/or target anatomy). For example, systems and devices described herein can be used to ablation via pulsed field ablation from inside the bile duct to treat a surrounding cholangiocarcinoma (liver tumor).

The systems, devices, and methods described herein can be embodied in one or more embodiments, as set forth below.

Embodiment 1: A catheter device for delivering pulsed field ablation with two sets of electrodes in a distal flexible portion comprising a first proximal set of electrodes and a second distal set of electrodes, with at least three electrodes in each set, with a first series of inter-electrode spacings between adjacent electrodes in the first set, with a second series of inter-electrode spacings between adjacent electrodes in the second set, and an inter-set spacing separating the first and second electrode sets, with the inter-set spacing being at least 50% larger than any of the inter-electrode spacings in the first or second electrode sets, with the first set of electrodes electrically jointly wired with a first electrical lead wire, and the second set of electrodes electrically jointly wired with a second electrical lead wire.

Embodiment 2: The catheter of Embodiment 1, where each lead wire is electrically insulated with at least one insulation layer capable of withstanding a voltage of at least about 300 Volts across its insulation thickness without dielectric breakdown.

Embodiment 3: The catheter of Embodiment 1, where at least one lead wire passes through a lumen in the catheter with the lumen wall capable of withstanding a voltage of at least about 300 Volts across its thickness without dielectric breakdown.

Embodiment 4: The catheter of Embodiment 1, where the inter-set spacing between first and second electrode sets is greater than about 3 mm.

Embodiment 5: The catheter of Embodiment 1, where the first set of electrodes and the second set of electrodes comprise at least 3 electrodes each.

Embodiment 6: The catheter of Embodiment 1, where the portion of the catheter shaft that is distal to the most distal electrode of the second set of electrodes is tapered such that the catheter shaft diameter progressively decreases along the distal direction.

Embodiment 7: The catheter of Embodiment 1, where the catheter includes a guidewire lumen such that the catheter may be inserted over a guidewire inserted into a vascular structure or other anatomical passageway of a subject anatomy.

Embodiment 8: The catheter of Embodiment 1, where the catheter shaft is deflectable.

Embodiment 9: The catheter of Embodiment 1, where the length of the first set of electrodes from proximal end of the most proximal electrode of the first set of electrodes to the distal end of the most distal electrode of the first set of electrodes is at least 3 times larger than the diameter of the catheter.

Embodiment 10: The catheter of Embodiment 1, where the length of the second set of electrodes from proximal end of the most proximal electrode of the second set to the distal end of the most distal electrode of the second set is at least 3 times larger than the diameter of the catheter.

Embodiment 11: The catheter of Embodiment 1, where during ablation delivery the first set of electrodes and the second set of electrodes have opposite electrical polarities for high voltage pulse delivery.

Embodiment 12: A catheter device for delivering pulsed field ablation. with two sets of electrodes in a distal flexible portion comprising a first proximal set of electrodes and a second distal set of electrodes, with at least three electrodes in each set, with at least one of the electrodes in the form of a basket electrode comprising superelastic material in a compressible configuration with the unstressed diameter of the basket electrode being larger than the shaft diameter of the catheter, with a first series of inter-electrode spacings between adjacent electrodes in the first set, with a second series of inter-electrode spacings between adjacent electrodes in the second set, and an inter-set spacing separating the first and second electrode sets, with the inter-set spacing being at least 50% larger than any of the inter-electrode spacings in the first or second electrode sets, with the first set of electrodes electrically jointly wired with a first electrical lead wire, and the second set of electrodes electrically jointly wired with a second electrical lead wire.

Embodiment 13: The catheter of Embodiment 12, where each basket electrode includes a collar portion for attachment to the catheter shaft and to an electrical lead wire.

Embodiment 14: The catheter of Embodiment 12, where each basket electrode is compressible to conform for passage through a vascular anatomy or other anatomical passageway with inner diameter smaller than the diameter of the basket electrode in its unstressed configuration.

Embodiment 15: The catheter of Embodiment 12, where each lead wire is electrically insulated with at least one insulation layer capable of withstanding a voltage of at least about 300 Volts across its insulation thickness without dielectric breakdown.

Embodiment 16: The catheter of Embodiment 12, where at least one lead wire passes through a lumen in the catheter with the lumen wall capable of withstanding a voltage of at least about 300 Volts across its thickness without dielectric breakdown.

Embodiment 17: The catheter of Embodiment 12, where the inter-set spacing between first and second electrode sets is greater than about 3 mm.

Embodiment 18: The catheter of Embodiment 12, where the first set of electrodes and the second set of electrodes comprise at least 3 electrodes each.

Embodiment 19: The catheter of Embodiment 12, where the portion of the catheter shaft that is distal to the most distal electrode of the second set of electrodes is tapered such that the catheter shaft diameter progressively decreases along the distal direction.

Embodiment 20: The catheter of Embodiment 12, where the catheter includes a guidewire lumen such that the catheter may be inserted over a guidewire inserted into a vascular structure or other anatomical passageway of a subject anatomy.

Embodiment 21: The catheter of Embodiment 12, where the catheter shaft is deflectable.

Embodiment 22: The catheter of Embodiment 12, where the length of the first set of electrodes from proximal end of the most proximal electrode of the first set of electrodes to the distal end of the most distal electrode of the first set of electrodes in the unstressed configuration of the electrodes is at least 3 times larger than the diameter of the catheter.

Embodiment 23: The catheter of Embodiment 12, where the length of the second set of electrodes from proximal end of the most proximal electrode of the second set of electrodes to the distal end of the most distal electrode of the second set of electrodes in the unstressed configuration of the electrodes is at least 3 times larger than the diameter of the catheter.

Embodiment 24: The catheter of Embodiment 12, where during ablation delivery the first set of electrodes and the second set of electrodes have opposite electrical polarities for high voltage pulse delivery.

Embodiment 25: A method for renal denervation comprising passage of a catheter with two sets of electrodes along its distal flexible portion, comprising a first proximal set of electrodes and a second distal set of electrodes, with at least three electrodes in each set, with a first series of inter-electrode spacings between adjacent electrodes in the first set, with a second series of inter-electrode spacings between adjacent electrodes in the second set, and an inter-set spacing separating the first and second sets of electrodes, with the inter-set spacing being at least 50% larger than any of the inter-electrode spacings in the first or second set of electrodes, positioning the distal portion of the catheter in a first vascular section or other anatomical passageway, delivering high voltage pulses to the first and second electrode sets for ablation in the first vascular section or other anatomical passageway, moving the catheter to position the distal portion of the catheter in a second vascular section or other anatomical passageway, and delivering high voltage pulses to the first and second electrode sets for ablation in the second vascular section or other anatomical passageway.

Embodiment 26: An apparatus, comprising: a shaft including a distal flexible portion; and a plurality of electrodes disposed on the distal flexible portion, the plurality of electrodes being wired to one or more lead wires and being configured to deliver pulsed field ablation, the plurality of electrodes including at least one basket electrode that is formed of a superelastic material, the basket electrode being configured to transition from an unstressed configuration to a stressed configuration by being compressed, the basket electrode in the unstressed configuration having a diameter greater than a diameter of the shaft, the basket electrode including: a collar portion that is attached to the shaft and to one of the one or more lead wires; and an open end opposite the collar portion that is configured to move or slide on the shaft as the basket electrode is compressed into the stressed configuration.

Embodiment 27: An apparatus, comprising: a catheter device including a distal portion; a first set of one or more electrodes disposed on the distal portion, the first set of electrodes being spaced from one another by a first set of inter-electrode spacings, the first set of electrodes being jointly wired to one another via a first lead wire; and a second set of one or more electrodes disposed on the distal portion distal to the first set of electrodes, the second set of electrodes being spaced from one another by a second set of inter-electrode spacings, the second set of electrodes being jointly wired to one another via a second lead wire, the first set of electrodes and the second set of electrodes including at least one basket electrode that is formed of a superelastic material and is configured to be compressed, the basket electrode including: a fixed end that is attached to the distal portion and to a respective one of the first and second lead wires; and an open end opposite the fixed end that is configured to move or slide on the distal portion as the basket electrode is compressed, the first and second sets of electrodes configured to deliver pulsed field ablation.

Embodiment 28: An apparatus, comprising: a catheter device including a distal portion; a first electrode disposed on the distal portion, the first electrode being coupled to a first lead wire; and a second electrode disposed on the distal portion distal to the first electrode, the second electrode being coupled a second lead wire, the first and second electrodes including at least one basket electrode that is formed of a superelastic material and is configured to be compressed, the basket electrode including: a fixed end that is attached to the distal portion and to a respective one of the first and second lead wires; and an open end opposite the fixed end that is configured to move or slide on the distal portion as the basket electrode is compressed, the first and second sets of electrodes configured to deliver pulsed field ablation.

Embodiment 29: A method, comprising: positioning a distal flexible portion of a catheter device in a first section of vascular anatomy or other anatomical passageway, the distal flexible portion having first and second sets of electrodes disposed thereon, at least the first set of electrodes or the second set of electrodes including at least one basket electrode that is formed of a superelastic material, the basket electrode including a fixed end that is attached to the distal flexible portion and an open end opposite the fixed end that is configured to move or slide on the distal flexible portion such that the basket electrode can be compressed based on a dimension of the vascular anatomy or other anatomical passageway in which the basket electrode is disposed; delivering high voltage pulses to the first and second electrode sets to ablate the first section of the vascular anatomy or other anatomical passageway; moving the distal flexible portion of the catheter to a second section of the vascular anatomy or other anatomical passageway; and delivering high voltage pulses to the first and second electrode sets to ablate the second section of the vascular anatomy or other anatomical passageway.

While specific examples have been provided in the figure for example and illustrative purposes, it should be clear that variants such as different numbers of lumens, different numbers of electrodes, electrode diameters, inter-electrode spacings, inter-set spacing and the like can be constructed without limitation and based on the teachings herein. Likewise, while the figures illustrating cage-like electrodes show specific examples of cage-like electrode configurations, it should be noted that a variety of strut geometries can be employed in the construction of such configurations.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The invention claimed is:

1. An apparatus, comprising:
   a shaft including a distal flexible portion; and
   a plurality of electrodes disposed on the distal flexible portion, the plurality of electrodes being wired to one or more lead wires and being configured to deliver pulsed field ablation, the plurality of electrodes including:
     a first set of one or more electrodes, the first set of electrodes including at least three electrodes that are spaced from one another by a first set of inter-electrode spacings, the first set of electrodes being jointly wired to one another via a first lead wire; and
     a second set of one or more electrodes disposed distal to the first set of electrodes, the second set of electrodes including at least three electrodes that are spaced from one another by a second set of inter-electrode spacings, the second set of electrodes being jointly wired to one another via a second lead wire,
   the first and second sets of electrodes configured to deliver the pulsed field ablation,
   the plurality of electrodes including at least one basket electrode that is formed of a superelastic and electrically conductive material, the basket electrode being configured to transition from an unstressed configuration to a stressed configuration by being compressed, the basket electrode in the unstressed configuration having a diameter greater than a diameter of the shaft,
   the basket electrode including:
     a collar portion that is attached to the shaft and to one of the one or more lead wires; and
     an open end opposite the collar portion that is configured to move or slide on the shaft as the basket electrode is compressed into the stressed configuration.

2. The apparatus of claim 1, wherein the second set of electrodes is spaced from the first set of electrodes by an inter-set spacing, the inter-set spacing being at least 50% greater than each inter-electrode spacing of the first and second sets of inter-electrode spacings.

3. The apparatus of claim 2, wherein the inter-set spacing between the first and second electrode sets is greater than about 3 mm.

4. The apparatus of claim 1, wherein a length of the first set of electrodes defined as a distance from a proximal end of the most proximal electrode of the first set of electrodes to a distal end of the most distal electrode of the first set of electrodes is at least about three times greater than a diameter of the shaft, and
   a length of the second set of electrodes defined as a distance from a proximal end of the most proximal electrode of the second set of electrodes to a distal end of the most distal electrode of the second set of electrodes is at least about three times greater than the diameter of the shaft.

5. The apparatus of claim 1, wherein the first and second sets of electrodes are configured to be energized with opposite electrical polarities to deliver the pulsed field ablation.

6. The apparatus of claim 1, wherein each of the first and second lead wires is electrically insulated with at least one insulation layer configured to withstand a voltage of at least about 300 Volts across a thickness of the at least one insulation layer without dielectric breakdown.

7. The apparatus of claim 1, further comprising a lumen wall defining a lumen, the one or more lead wires being disposed in the lumen, and the lumen wall configured to withstand a voltage of at least about 300 Volts across a thickness of the lumen wall without dielectric breakdown.

8. The apparatus of claim 1, wherein the shaft includes a tapered portion that tapers in a distal direction, the tapered portion being distal to the most distal electrode of the plurality of electrodes.

9. The apparatus of claim 1, wherein the shaft defines a guidewire lumen such that the shaft can be inserted in an anatomical passageway of a subject anatomy over a guidewire.

10. The apparatus of claim 1, wherein the shaft is deflectable.

11. The apparatus of claim 1, wherein a length of the plurality of electrodes defined as a distance from a proximal end of the most proximal electrode of the plurality of electrodes to a distal end of the most distal electrode of the plurality of electrodes is at least about three times greater than a diameter of the shaft.

12. An apparatus, comprising:

a catheter device including a distal portion;

a first set of one or more electrodes disposed on the distal portion, the first set of electrodes being spaced from one another by a first set of inter-electrode spacings, the first set of electrodes being jointly wired to one another via a first lead wire; and a second set of one or more electrodes disposed on the distal portion distal to the first set of electrodes, the second set of electrodes being spaced from one another by a second set of inter-electrode spacings, the second set of electrodes being jointly wired to one another via a second lead wire, the first set of electrodes and the second set of electrodes including at least one basket electrode that is formed of a superelastic and electrically conductive material and is configured to be compressed, the basket electrode including:

a fixed end that is attached to the distal portion and to a respective one of the first and second lead wires; and an open end opposite the fixed end that is configured to move or slide on the distal portion as the basket electrode is compressed, the first and second sets of electrodes configured to deliver pulsed field ablation.

13. The apparatus of claim 12, wherein each of the first and second sets of electrodes includes at least two basket electrodes.

14. The apparatus of claim 12, wherein each basket electrode is compressible such that basket electrode can conform to an inner diameter of an anatomical passageway or a sheath that is smaller than a diameter of that basket electrode in an unstressed configuration to be advanced through the anatomical passageway.

15. The apparatus of claim 12, wherein each of the first and second lead wires is electrically insulated with at least one insulation layer configured to withstand a voltage of at least about 300 Volts across a thickness of the at least one insulation layer without dielectric breakdown.

16. The apparatus of claim 12, wherein the second set of electrodes is spaced from the first set of electrodes by an inter-set spacing, the inter-set spacing being at least 50% greater than each inter-electrode spacing of the first and second sets of inter-electrode spacings.

17. The apparatus of claim 12, wherein the catheter device includes a shaft, the shaft including a tapered portion that tapers in a distal direction, the tapered portion being distal to the most distal electrode of the second set of electrodes.

18. An apparatus, comprising:

a catheter device including a distal portion;

a first electrode disposed on the distal portion, the first electrode being coupled to a first lead wire; and a second electrode disposed on the distal portion distal to the first electrode, the second electrode being coupled a second lead wire, the first and second electrodes including at least one basket electrode that is formed of a superelastic and electrically conductive material and is configured to be compressed, the basket electrode including:

a fixed end that is attached to the distal portion and to a respective one of the first and second lead wires; and an open end opposite the fixed end that is configured to move or slide on the distal portion as the basket electrode is compressed, the first and second electrodes configured to deliver pulsed field ablation.

19. The apparatus of claim 12, wherein the first and second sets of electrodes are configured to be energized with opposite electrical polarities to deliver the pulsed field ablation.

20. The apparatus of claim 17, wherein a length of the first set of electrodes is defined as a distance from a proximal end of the most proximal electrode of the first set of electrodes to a distal end of the most distal electrode of the first set of electrodes is at least about three times greater than a diameter of the shaft.

21. The apparatus of claim 17, wherein a length of the second set of electrodes is defined as a distance from a proximal end of the most proximal electrode of the second set of electrodes to a distal end of the most distal electrode of the second set of electrodes is at least about three times greater than a diameter of the shaft.

22. The apparatus of claim 18, wherein the basket electrode is compressible such that basket electrode can conform to an inner diameter of an anatomical passageway or a sheath that is smaller than the diameter of that basket electrode in an unstressed configuration to be advanced through the anatomical passageway.

23. The apparatus of claim 18, wherein the first and second electrodes are configured to be energized with opposite electrical polarities to deliver the pulsed field ablation.

24. The apparatus of claim 18, wherein each of the first and second lead wires is electrically insulated with at least one insulation layer configured to withstand a voltage of at least about 300 Volts across a thickness of the at least one insulation layer without dielectric breakdown.

25. The apparatus of claim 18, wherein the catheter device includes a shaft, the shaft including a tapered portion that tapers in a distal direction, the tapered portion being distal to the second electrode.

26. A method, comprising:

positioning a distal flexible portion of a catheter device in a first section of an anatomical passageway, the distal flexible portion having first and second sets of electrodes disposed thereon, at least the first set of electrodes or the second set of electrodes including at least one basket electrode that is formed of a superelastic and electrically conductive material, the basket electrode including a fixed end that is attached to the distal flexible portion and an open end opposite the fixed end that is configured to move or slide on the distal flexible portion such that the basket electrode can be compressed based on a dimension of the anatomical passageway in which the basket electrode is disposed;

delivering high voltage pulses to the first and second electrode sets to ablate the first section of the anatomical passageway;

moving the distal flexible portion of the catheter to a second section of the anatomical passageway; and delivering high voltage pulses to the first and second electrode sets to ablate the second section of the anatomical passageway.

27. The method of claim 26, further comprising, in response to moving the distal flexible portion of the catheter, causing the basket electrode to compress or expand based on the dimension of the anatomical passageway that the basket electrode traverses.

28. The method of claim 27, wherein moving the distal flexible portion of the catheter to a second section of the anatomical passageway includes retracting the distal flexible portion of the catheter, and in response to retracting the distal flexible portion of the catheter, causing the basket electrode to automatically expand.

29. The method of claim 26, wherein delivering high voltage pulses to the first and second electrode sets includes delivering pulses of opposite electrical polarities to the first and second electrode sets.

* * * * *